United States Patent [19]

Blaszczak et al.

[11] Patent Number: 4,983,732

[45] Date of Patent: Jan. 8, 1991

[54] METHOD OF DEPROTECTION OF 3-AMINO AZETIDINONES

[75] Inventors: Larry C. Blaszczak; John E. Munroe, both of Indianapolis; Douglas O. Spry, Mooresville, all of Ind.

[73] Assignee: Eli Lilly and Company, Indianapolis, Ind.

[21] Appl. No.: 410,208

[22] Filed: Sep. 21, 1989

Related U.S. Application Data

[62] Division of Ser. No. 80,354, Jul. 31, 1987, abandoned.

[51] Int. Cl.$^5$ ............... C07B 511/00; C07D 205/095; C07D 205/085; C07D 471/04
[52] U.S. Cl. ............................ 540/360; 540/205; 540/222; 540/224; 540/226; 540/229; 540/230; 540/363; 540/364; 560/11; 560/17
[58] Field of Search ............... 540/360, 363, 364

[56] References Cited

U.S. PATENT DOCUMENTS 3,842,077 10/1974 Henniger ..................... 260/243 C
4,052,387 10/1977 Kukolja ........................ 540/359

FOREIGN PATENT DOCUMENTS 0109302 5/1984 European Pat. Off. .
0138113 4/1985 European Pat. Off. .
8800941 2/1988 PCT Int'l Appl. .
1134682 11/1968 United Kingdom .
1438422 6/1976 United Kingdom .

OTHER PUBLICATIONS

Micetich et al., *Synth. Comm.*, 116(4) 453–460 (1986).
Grehn, *J. Chem. Soc. Chem. Comm.*, 1985, p. 1317.

*Primary Examiner*—Mark L. Berch
*Attorney, Agent, or Firm*—James J. Sales; Leroy Whitaker

[57] ABSTRACT

A method for preparing 2-amino-$\beta$-lactams which are substituted by readily-removed protecting groups is provided. According to this invention, an acyl-2-amino-$\beta$-lactam is further acylated with a different acyl group and is subsequently treated with base to provide a protected 2-amino $\beta$-lactam with allyloxycarbonyl, t-butoxycarbonyl, naphthyloxycarbonyl, trichloroethyloxycarbonyl, p-nitrobenzyloxycarbonyl, benzhydryloxycarbonyl, p-methoxybenzyloxycarbonyl, or o-nitrobenzyloxycarbonyl.

3 Claims, No Drawings

METHOD OF DEPROTECTION OF 3-AMINO AZETIDINONES

This application is a division of application Ser. No. 07/080,354, filed July 31, 1987 abandoned.

BACKGROUND OF THE INVENTION

The clinically useful $\beta$-lactam antibiotics include a wide variety of compounds: cephalosporins such as cephalexin, cefaclor, and cefamandol; totally synthetic "oxa"-cephalosporins such as moxalactam; and a variety of monocyclic $\beta$-lactams as well as bicyclic $\beta$-lactams. Because the $\beta$-lactam antibiotics represent such an important therapeutic class, considerable effort is directed toward more efficient methods for their preparation.

SUMMARY

This invention relates to a process for preparing $\beta$-lactam antibiotic intermediates. In particular, it relates to a process for the selective N-deacylation of an N-(alkyl, arylalkyl, or alkenyl)oxycarbonyl N-acylamino substituted $\beta$-lactam to an N-(alkyl, arylalkyl, or alkenyl)oxycarbonylamino substituted $\beta$-lactam. The process affords ready exchange of the N-acyl group of an N-acylamino substituted $\beta$-lactam to a protected amino substituted $\beta$-lactam wherein the amino-protecting group is readily removable. The process thus provides protected-amino substituted $\beta$-lactam compounds which, upon deprotection, afford free amino substituted $\beta$-lactams. The latter are valuable intermediates to antibiotic compounds.

In an example of the process, p-nitrobenzyl 7$\beta$-phenoxyacetylamino-3-methyl-3-cephem-4-carboxylate is reacted in an inert solvent with di-t-butyldicarbonate in the presence of 4-dimethylaminopyridine to form p-nitrobenzyl 7$\beta$-[(N-t-butyloxycarbonyl-N-phenoxyacetyl)amino]-3-methyl-3-cephem-4-carboxylate. The latter is treated in an inert solvent at room temperature with N,N-diethylethylene diamine to provide p-nitrobenzyl 7$\beta$-(t-butyloxycarbonylamino)-3-methyl-3-cephem-4-carboxylate.

Also provided by this invention are novel disubstituted-amino substituted $\beta$-lactams.

The process provided herein is an alternative method to known N-deacylation methods employed with $\beta$-lactam compounds. For example, there are instances when the known imino halide, imino ether cleavage method results in low yields or undue decomposition. In such cases, the present process can be an attractive alternative.

DETAILED DESCRIPTION OF THE INVENTION

The present invention provides a process for preparing a protected amino substituted $\beta$-lactam compound of Formula (1)

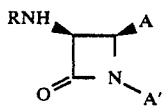
(1)

wherein R is allyloxycarbonyl, t-butoxycarbonyl, naphthyloxycarbonyl, trichloroethyloxycarbonyl, p-nitrobenzyloxcarbonyl, benzhydryloxycarbonyl, p-methoxybenzyloxcarbonyl, o-nitrobenzyloxycarbonyl or acetoxy; wherein A and A', when taken separately, are defined as follows:

A is $C_1$ to $C_6$ alkyl, $C_1$ to $C_6$ substituted alkyl or a group of the formula $-S(C_1-C_4)CO_2R'$, wherein R' is hydrogen or a carboxy-protecting group;

A' is hydrogen or an amide-protecting group; and when A and A' are taken together, they form a group of the formula

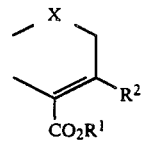

wherein $R^1$ is a carboxy-protecting group; X is sulfur, $-CH_2-$, or oxygen and $R^2$ is hydrogen or a substituent group as defined hereinafter; which comprises:

reacting of a compound of Formula (2):

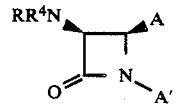
(2)

wherein A and A' are the same as defined hereinabove and $R^4$ is phenoxyacetyl, phenylacetyl, $C_1-C_6$ alkanoyl, or chloroacetyl; with a suitable base, in an inert solvent or when $R^4$ is chloroacetyl, with thiourea.

The process is carried out at temperatures between about 0° C. and about 50° C., preferably at about 25° C.

Inert solvents which can be used include, for example, tetrahydrofuran, ethyl acetate, halogenated hydrocarbons such as methylene chloride, di- or trichloroethane and the like.

In the above formulae, $R^2$ is hydrogen, halo, $C_1-C_6$ alkoxy, $C_1$ to $C_6$ alkyl, $C_1$ to $C_6$ substituted alkyl, $C_1$ to $C_6$ alkylthio, $C_1-C_6$ substituted alkylthio, $C_7$ to $C_{12}$ arylalkyl, $C_7$ to $C_{12}$ substituted arylalkyl, phenyl or substituted phenyl; a group of the formula

wherein X is fluoro, chloro, bromo, or iodo; a group of the formula

wherein $R^6$ is hydrogen, $C_1$ to $C_6$ alkyl, $C_1$ to $C_6$ substituted alkyl, $C_7$ to $C_{12}$ arylalkyl, $C_7$ to $C_{12}$ substituted arylalkyl, phenyl, substituted phenyl, amino, (monosubstituted)amino, or (disubstituted)amino; a group of the formula

wherein $R^7$ is hydrogen, an organic or inorganic cation, $C_1$ to $C_6$ alkyl, $C_1$ to $C_6$ substituted alkyl, $C_7$ to $C_{12}$ arylalkyl, $C_7$ to $C_{12}$ substituted arylalkyl, phenyl, substituted phenyl, a carboxy-protecting group, or a nontoxic, metabolically-labile, ester-forming group; a group of the formula $-CH_2-S-$"Heterocyclic"; a group of the formula $-S-$ "heterocyclic"; a group of the formula $-OR^9$ wherein $R^9$ is hydrogen, $C_1$ to $C_6$ alkyl, $C_1$ to $C_6$ substituted alkyl, $C_7$ to $C_{12}$ arylalkyl, $C_7$ to $C_{12}$ substituted arylalkyl, phenyl, substituted phenyl or $C_1$ to $C_7$ acyl.

A preferred embodiment of this invention is the process wherein A and A' are taken together and form a group of the formula

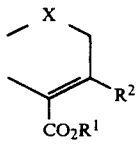

A preferred embodiment of this invention is the process wherein X is —CH$_2$— or sulfur.

An especially preferred embodiment of this invention is the process wherein X is —CH$_2$—.

In the above Formulae, the term "C$_1$ to C$_6$ alkyl" denotes such radicals as methyl, ethyl, n-propyl, isopropyl, n-butyl, sec-butyl, tert-butyl, amyl, tert-amyl, hexyl and the like. The preferred "C$_1$ to C$_6$ alkyl" group is methyl.

The term "C$_1$ to C$_6$ substituted alkyl" denotes the above C$_1$ to C$_6$ alkyl groups that are substituted by one or two halogen, hydroxy, protected hydroxy, amino, protected amino, C$_1$ to C$_7$ acyloxy, nitro, carboxy, protected carboxy, carbamoyl, carbamoyloxy, cyano, methylsulfonylamino or C$_1$ to C$_4$ alkoxy groups. The substituted alkyl groups may be substituted once or twice with the same or with different substituents.

Examples of the above substituted alkyl groups include the cyanomethyl, nitromethyl, hydroxymethyl, trityloxymethyl, propionyloxymethyl, aminomethyl, carboxymethyl, allyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, 6-hydroxyhexyl, 2,4-dichloro(n-butyl), 2-amino(iso-propyl), 2-carbamoyloxyethyl and the like. A preferred group of examples within the above "C$_1$ to C$_6$ substituted alkyl" group includes the substituted methyl group, e.g., a methyl group substituted by the same substituents as the "C$_1$ to C$_6$ substituted alkyl" group. Examples of the substituted methyl group include groups such as hydroxymethyl, protected hydroxymethyl, (e.g., tetrahydropyranyloxymethyl), acetoxymethyl, carbamoyloxymethyl, chloromethyl, bromomethyl and iodomethyl.

The term "C$_1$ to C$_4$ alkoxy" as used herein denotes groups such as methoxy, ethoxy, n-propoxy, isopropoxy, n-butoxy, t-butoxy and like groups. The term "C$_1$ to C$_7$ acyloxy" denotes herein groups such as formyloxy, acetoxy, propionyloxy, butyryloxy, pentanoyloxy, hexanoyloxy, heptanoyloxy, and the like. Similarly, the term "C$_1$ to C$_7$ acyl" encompasses groups such as formyl, acetyl, propionyl, butyryl, pentanoyl, hexanoyl, heptanoyl, benzoyl and the like.

The term "substituted phenyl" specifies a phenyl group substituted with one or two moieties chosen from the group consisting of halogen, hydroxy, protected hydroxy, cyano, nitro, C$_1$ to C$_6$ alkyl, C$_1$ to C$_4$ alkoxy, carboxy, protected carboxy, carboxymethyl, protected carboxymethyl, hydroxymethyl, protected hydroxymethyl, aminomethyl, protected aminomethyl, trifluoromethyl or N-(methylsulfonylamino).

Examples of the term "substituted phenyl" include a mono- or di(halo)phenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-(iso-propyl)phenyl, 4-ethylphenyl, 3-(n-propyl)phenyl and the like; a mono- or di(alkoxy)phenyl group, for example, 2,6-dimethoxyphenyl, 4-methoxyphenyl, 3-ethoxyphenyl, 4-(isopropoxy)phenyl, 4-(t-butoxy)phenyl, 3-ethoxy-4-methoxyphenyl and the like; 3- or 4- trifluoromethylphenyl; a mono- or dicarboxyphenyl or (protected carboxy)phenyl group such as 4-carboxyphenyl or 2,4-di(-protected carboxy)phenyl; a mono- or di(hydroxymethyl)phenyl or (protected hydroxymethyl)phenyl such as 3-(protected hydroxymethyl)phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)-phenyl; or a mono- or di(N-(methylsulfonylamino))phenyl such as 3-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like. Preferred substituted phenyl groups include the 2- and 3-trifluoromethylphenyl, the 4-hydroxyphenyl, the 2-aminomethylphenyl and the 3-(N-(methylsulfonylamino))phenyl groups.

When the various groups which comprise the R$^2$ definition include an amino and/or hydroxy moiety, it is desirable that said amino and/or hydroxy moiety will be suitably protected using methodology known per se in the art in order to prevent unwanted O- or N-acylation.

The terms "halo" and "halogen" refer to the fluoro, chloro, bromo or iodo groups. Chloro is preferred.

The term "trihalomethyl" denotes trifluoromethyl, trichloromethyl, tribromomethyl or triiodomethyl.

The terms C$_1$ to C$_6$ alkylthio and C$_1$ to C$_6$ substituted alkylthio denote C$_1$ to C$_6$ alkyl and C$_1$ to C$_6$ substituted alkyl groups, respectively, attached to a sulfur which is in turn the point of attachment for the C$_1$ to C$_6$ alkylthio or C$_1$ to C$_6$ substituted alkylthio group.

The term "C$_7$ to C$_{12}$ arylalkyl" denotes a C$_1$ to C$_6$ alkyl group substituted at any position by a phenyl ring. Examples of such a group include phenyl methyl (benzyl), 2-phenylethyl, 3-phenyl-(n-propyl), 4-phenylhexyl, 3-phenyl-(n-amyl), 3-phenyl-(sec-butyl), and the like. A preferred group is the benzyl group.

The term "C$_7$ to C$_{12}$ substituted arylalkyl" denotes a C$_7$ to C$_{12}$ arylalkyl group substituted on the C$_1$ to C$_6$ alkyl portion with one or two groups chosen from halogen, hydroxy, protected hydroxy, amino, protected amino, C$_1$ to C; acyloxy, nitro, carboxy, protected carboxy, carbamoyl, carbamoyloxy, cyano, C$_1$ to C$_6$ alkylthio, N-(methylsulfonylamino) or C$_1$ to C$_4$ alkoxy; and/or the phenyl group may be substituted with 1 or 2 groups chosen from halogen, hydroxy, protected hydroxy, nitro, C$_1$ to C$_6$ alkyl, C$_1$ to C$_4$ alkoxy, carboxy, protected carboxy, carboxymethyl, protected carboxymethyl, hydroxymethyl, protected hydroxymethyl, aminomethyl, protected aminomethyl, or an N-(methylsulfonylamino) group. As before, when either the C$_1$ to C$_6$ alkyl portion or the phenyl portion or both are disubstituted, the substituents can be the same or different.

Examples of the term "$C_7$ to $C_{12}$ substituted arylalkyl" include groups such as 2-phenyl-1-chloroethyl, 2-(4-methoxyphenyl)ethyl, 2,6-dihydroxy-4-phenyl(n-hexyl), 5-cyano-3-methoxy-2-phenyl(n-pentyl), 3-(2,6-dimethylphenyl)n-propyl, 4-chloro-3-aminobenzyl, 6-(4-methoxyphenyl)-3-carboxy(n-hexyl), 5-(4-aminomethyl phenyl)-3-(aminomethyl)(n-pentyl), and the like.

The term "(monosubstituted)amino" refers to an amino group with one substituent chosen from the group consisting of phenyl, substituted phenyl, $C_1$ to $C_6$ alkyl, and $C_7$ to $C_{12}$ arylalkyl, wherein the latter three substituent terms are as defined above.

The term "(disubstituted)amino" refers to amino groups with two substituents chosen from the group consisting of phenyl, substituted phenyl, $C_1$ to $C_6$ alkyl, and $C_7$ to $C_{12}$ arylalkyl wherein the latter three substituent terms are as described above. The two substituents can be the same or different.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4''-trimethoxytrityl, 2-phenylprop-2-yl, trimethylsilyl, t-butyldimethylsilyl, phenacyl, 2,2,2-trichloroethyl, β-(trimethylsilyl)ethyl, β-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other positions of the β-lactam molecule and can be removed at the appropriate point without disrupting the remainder of the molecule. In particular, it is important not to subject the carboxy-protected β-lactam molecule to strong nucleophilic bases or reductive conditions employing highly activated metal catalysts such as Raney nickel. (Such harsh removal conditions are also to be avoided when removing amino-protecting groups and hydroxy-protecting groups, discussed below.) Preferred carboxylic acid protecting groups are the allyl and p-nitrobenzyl groups. Similar carboxy-protecting groups used in the cephalosporin, penicillin and peptide arts can also be used to protect a carboxy group substituents of the β-lactam. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. A related term is "protected carboxy", which refers to a carboxy group substituted with one of the above carboxy-protecting groups.

The term "heterocyclic" denotes optionally substituted 5-membered or 6-membered rings that have 1 to 4 heteroatoms, such as oxygen, sulfur and/or nitrogen, in particular nitrogen, either alone or in conjunction with sulfur or oxygen ring atoms. These 5-membered or 6-membered rings may be fully unsaturated or partially unsaturated, with fully unsaturated rings being preferred.

Furthermore, the above optionally substituted 5-membered or 6-membered rings can optionally be fused to an aromatic 5-membered or 6-membered ring system. For example, the rings can be optionally fused to an aromatic 5-membered or 6-membered ring system such as a pyridine or a triazole system, and preferably to a benzene ring.

The following ring systems are examples of the heterocyclic (whether substituted or unsubstituted) radicals denoted by the term "heterocyclic": thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo[1,5-b]pyridazinyl and purinyl, as well as benzo-fused derivatives, for example benzoxazolyl, benzthiazolyl, benzimidazolyl and indolyl.

Preferred heterocyclic rings are 5-membered ring systems containing a sulfur or oxygen atom and one to three nitrogen atoms. Examples of such preferred groups include thiazolyl, in particular thiazol-2-yl and thiazol-2-yl N-oxide, thiadiazolyl, in particular 1,3,4-thiadiazol-5-yl and 1,2,4-thiadiazol-5-yl, oxazolyl, preferably oxazol-2-yl, and oxadiazolyl, such as 1,3,4-oxadiazol-5-yl, and 1,2,4-oxadiazol-5-yl. A group of further preferred examples of 5-membered ring systems with 2 to 4 nitrogen atoms include imidazolyl, preferably imidazol-2-yl; triazolyl, preferably 1,3,4-triazol-5-yl; 1,2,3-triazol-5-yl, 1,2,4-triazol-5-yl, and tetrazolyl, preferably 1H-tetrazol-5-yl. A preferred group of examples of benzo-fused derivatives are, in particular, benzoxazol-2-yl, benzthiazol-2-yl and benzimidazol-2-yl.

Further specific examples of the above heterocyclic ring systems are 6-membered ring systems containing one to three nitrogen atoms. Such examples include pyridyl, such as pyrid-2-yl, pyrid-3-yl and pyrid-4-yl; pyrimidyl, preferably pyrimid-2-yl and pyrimid-4-yl; triazinyl, preferably 1,3,4-triazin-2-yl and 1,3,5-triazin-4-yl; pyridazinyl, in particular pyridazin-3-yl, and pyrazinyl. The pyridine N-oxides and pyridazine N-oxides, and the pyridyl, pyrimid-2-yl, pyrimid-4-yl, pyridazinyl and the 1,3,4-triazin-2-yl radicals, are a preferred group.

The substituents for the optionally substituted heterocyclic ring systems, and further examples of the 5- and 6- membered ring systems discussed above, are found in W. Dürckheimer et al., U.S. Pat. No. 4,278,793, issued July 14, 1981, columns 9 through 21 and columns 33 through 188, herein incorporated by reference. (In columns 33 through 188, examples of the term "heterocyclic" are included in the heterocyclic thiomethyl groups listed under heading "A".)

A particularly preferred group of "heterocyclics" is 1,3-thiazol-2-yl, 4-(carboxymethyl)-5-methyl-1,3-thiazol-2-yl, 4-(carboxymethyl)-5-methyl-1,3-thiazol-2-yl sodium salt, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-carboxy-4-methyl-1,3,4-triazol-5-yl sodium salt, 2-carboxy-4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-methyl-1,3,4-thiadiazol-5-yl, 2-thiol-1,3,4- thiadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 2-methyl-1H-tetrazol-5-yl, 1,2,3-triazol-5-yl, 1-methyl-1,2,3-triazol-5-yl, 2-methyl-1,2,3-triazol-5-yl, 4-methyl-1,2,3-triazol-5-yl, pyrid-2-yl N-oxide, 6-methoxy-2-(N-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-triazin-3-yl, 1,4,5,6-tetrahydro-4-(formylmethyl)-5,6-dioxo-as-triazin-3-yl, 2,5-dihydro-5-oxo-6-hydroxy-as-triazin-3-yl, 2,5-dihydro-5-oxo-6-hydroxy-as-triazin-3-yl sodium salt, 2,5-dihydro-5-oxo-6-hydroxy-2-methyl-as-triazin-3-yl sodium salt, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5-dihydro-5-oxo-2,6-dimethyl-as-triazin-3-yl, tetrazolo-[1,5-b]pyridazin-6-yl and 8-aminotetrazolo[1,5-b]-pyridazin-6-yl.

A most preferred group of "heterocyclics" is 4-(carboxymethyl)-5-methyl-1,3-thiazol-2-yl, 4-(carboxymethyl)-5-methyl-1,3-thiazol-2-yl sodium salt, 1,3,4-triazol-5-yl, 2-methyl-1,3,4-triazol-5-yl, 1H-tetrazol-5-yl, 1-methyl-1H-tetrazol-5-yl, 1-(1-(dimethylamino)-eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl- sodium salt, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl sodium salt, 2,5-dihydro-5-oxo-6-hydroxy-2-methyl-as-triazin-3-yl, tetrazolo[1,5-b]pyridazin-6-yl, and 8-aminotetrazolo[1,5-b]pyridazin-6-yl.

As used herein, the term "amide-protecting group" refers to any group typically used in the β-lactam art for protecting the β-lactam ring nitrogen from undesirable side reactions. Such groups include p-methoxyphenyl, 3,4-dimethox-ybenzyl, benzyl, O-nitrobenzyl, di-(p-methoxyphenyl)methyl, triphenylmethyl, (p-methoxyphenyl)diphenylmethyl, diphenyl-4-pyridylmethyl, m-2-(picolyl)-N'-oxide, 5-dibenzosuberyl, trimethylsilyl, t-butyl dimethylsilyl, and the like. Further descriptions of the utility of these protecting groups can be found in "Protective Groups in Organic Synthesis", by Theodora W. Greene, 1981, John Wiley & Sons, New York.

The term "suitable base" refers to primary or secondary amines or an alkali metal hydroxide. Such suitable bases which can be used as selective nucleophiles include $C_1$–$C_7$ primary and $C_2$–$C_{14}$ secondary amines such as methylamine, ethylamine, propylamine, butylamine, pentylamine, hexylamine, heptylamine, dimethylamine, diethylamine, dipropylamine, dibutylamine, dipentylamine, dihexylamine, diheptyl, methylethylamine, methylpropylamine, methylbutylamine, methylpentylamine, methylhexylamine, methylheptylamine, ethylpropylamine, ethylbutylamine, ethylpentylamine, ethylhexylamine, ethylheptylamine, propylbutylamine, propylpentylamine, propylhexylamine, propylheptylamine, benzylamine, and the like. Further examples of secondary amines include tetrahydropyrazole, piperidine, and the like. Also included are the diamines such as N,N-diethylethylenediamine, and the like.

Preferred "suitable bases" include lithium hydroxide and N,N-diethylethylene diamine.

In the process provided by this invention, an acylamino-substituted β-lactam is first acylated to provide a diacylamino-substituted β-lactam which is then treated with a suitable base to provide the protected amino monosubstituted β-lactam represented by Formula (1) in which the original acyl substituent has been interchanged for a different and more dynamic protecting group.

For example, a compound of the formula

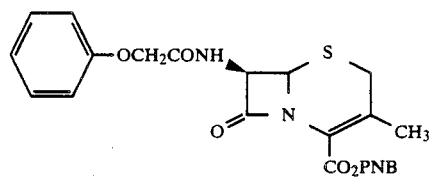

is acylated with di-t-butyldicarbonate in the presence of base to provide a compound of the formula

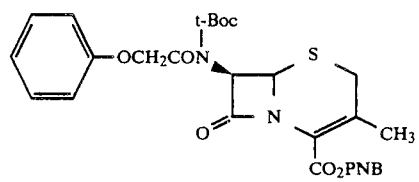

(t-BOC = t-butoxy carbonyl)

This imide can then be treated with a suitable base, for example, N,N-diethylethylene diamine, to provide a compound of the formula

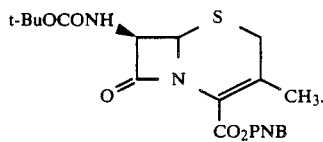

Accordingly, the phenoxyacetyl group or any other of several acetyl or substituted acetyl groups can be removed in a facile manner by first synthesizing the imide of Formula (2) followed by reaction with a suitable base.

Further, when the amide substitutent (R) is chloroacetyl, the resulting imide (2) can be treated with thiourea to provide the desired protected amino substituted β-lactam (1).

Temperature for formation of the imide should not be so high as to cause decomposition of the β-lactam substrate, but is not otherwise critical, so long as sufficient heat is present for the acylation to occur. It is preferable that the temperature be between about 0° C. and about 80° C.

The presence of a base is also desirable for the formation of the imide via deprotonation of the amino β-lactam. Such bases which are used typically include potassium hydroxide, sodium hydroxide and triethylamine. Choice of a base in this context is also dictated by the relative reactivity of the β-lactam substrate to undesired nucleophilic side reactions.

The original β-lactam amide substituent is typically an acyl group such as phenoxyacetyl, phenylacetyl, chloroacetyl or any such substituted or unsubstituted acetyl group. As such, removal of the original amino substituent using known procedures may, at times, either not work at all, or work, but at the same time be deleterious to other reactive sites on the β-lactam substrate.

Thus, it would be desirable of one of the above acetyl or substituted acetyl groups can be removed in a facile manner, while retaining the integrity of the β-lactam substrate.

In the present invention, it is preferred that the original substituted amino-β-lactam be acylated with a compound of the formula (R)$_2$O or R-L, in the presence of a base, wherein L is a suitable leaving group. Typical leaving groups (L) include bromo, iodo, chloro, imidazole, and the like. Although many acylating agents of the formula (R)$_2$O or R-L would be efficacious, di-t-butyl-dicarbonate is preferred.

The imide can then be treated with a suitable base, as described herein, to provide a compound of Formula (1). This displacement can be carried out in many polar organic solvents such as tetrahydrofuran, CH$_2$Cl$_2$, ethanol, propanol, butanol, dichloroethane, dioxane, ethyl acetate, and the like. Preferred solvents are tetrahydrofuran and CH$_2$Cl$_2$.

After a relatively short reaction time, typically 5 minutes to 2 hours, the desired product can be isolated by conventional methods and purified by chromatography over silica gel, if necessary.

The result of the process of this invention is thus an amino-substituted β-lactam substrate which is protected on the amino nitrogen with a more dynamic protecting group. For example, if R=t-butoxycarbonyl, one need only treat the β-lactam substrate with an acid such as trifluoroacetic acid followed by treatment with base to provide the free amino-substituted β-lactam in good yield. The process of this invention offers yet another solution to the problem of manipulation of protecting groups on the relatively sensitive amino-substituted β-lactam system and thus aids in the synthesis of clinically useful β-lactam antibiotics.

As one aspect of this invention, when X is sulfur, the resulting product may sometimes contain a mixture of Δ$^2$ and Δ$^3$ isomers. This problem may be overcome by simply employing the the procedure outlined by G. V. Kaiser, et al., *J. Org. Chem.*, 35, 2430 (1970). See also, "Cephalosporins and Penicillins" edited by Edwin H. Flynn, pp. 144-151, Academic Press(1972). According to this well-known method, a Δ$^2$ cephem can be oxidized to its corresponding sulfoxide, and in the process, the cephem bond is isomerized back to the Δ$^3$ isomer.

Thus, as a further aspect of this invention, there are provided novel intermediates of Formula (2),

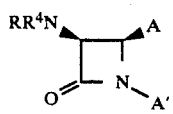

(2)

wherein R, R$^4$, A and A' are as defined above.

The class of suitable β-lactam substrates as defined in Formula (2) are rather numerous, the only limitation being stability under the relatively mild reaction conditions of the present invention.

Typical examples of β-lactam substrates include, but are not limited to, the monobactams, cephalosporins, oxacephalosporins such as moxalactam, and 1-carba(dethia)cephalosporins.

The monobactams, cephalosporins, and oxacephalosporins have been broadly disclosed and the necessary syntheses are known to one skilled in the β-lactam art. The 1-carba(dethia)cephalosporins have also been disclosed, but perhaps to a lesser degree. Thus, the synthesis of a particular class of 1-carba(dethia)cephalosporins is described below. (For a more complete description, see copending application, U.S. Ser. No. 066,908.)

Examples of one class of the 1-carbacephalosporins which are viable substrates for the process of this invention can be prepared by reacting a 3β-protected amino-4β-(2-substituted-ethyl)azetidin-2-one represented by Formula (AA):

(AA)

wherein R$^o$ represents an amino group substituted by a conventional amino-protecting group such as R or R$^4$ above, and T is a leaving group such as bromo, iodo, methanesulfonyloxy, trifluoromethylsulfonyloxy, or p-toluenesulfonyloxy, with a phenylsulfinyl or phenylsulfonyl substituted acrylic acid ester represented by Formula (BB):

(BB)

wherein A" is hydrogen, amino, C$_1$ to C$_6$ alkyl, C$_1$ to C$_6$ substituted alkyl, C$_7$ to C$_{12}$ arylalkyl, C$_7$ to C$_{12}$ substituted arylalkyl, phenyl or substituted phenyl, k is 1 or 2, and R$^1$ is as defined above, to provide a 7β-protected amino-1-carba-3-cephem ester represented by Formula (3):

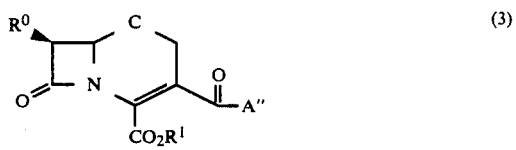

(3)

The condensation of (AA) with (BB) is preferably carried out in an inert aprotic solvent under substantially anhydrous conditions at a temperature between about −90° C. and about −45° C. with a strong non-nucleophilic base.

Inert aprotic solvents which can be used are aprotic organic solvents, for example, tetrahydrofuran, tetrahydropyran, dioxane, acetonitrile, diethyl ether, dimethylformamide, dimethylacetamide, 1,2-dimethoxyethane, and like solvents. Mixtures of such solvents may be used.

Non-nucleophilic bases which can be used include the silylated lithium amides such as bis(tri-C$_1$-C$_4$ alkylsilyl)lithium amides, e.g., bis-(trimethylsilyl)lithium amide, lithium diisopropylamide (LDA), sodium or potassium hexamethyldisilazide, and like bases.

For best results, the base, the acrylic acid ester (BB), and the 4-(2-substituted-ethyl)azetidinone (AA) are used in about equimolar amounts.

The process is carried out by first adding the nonnucleophilic base to a cold solution of (AA), in an inert solvent. The solution is stirred in the cold for a time sufficient to allow generation of the anion formed with the base and the azetidinone nitrogen. Generally, the mixture is stirred in the cold for about 20 minutes to about one hour. Next, the phenylsulfinyl acrylic acid ester, (BB), or a solution thereof in an inert aprotic solvent is added to the cold basic solution. The reaction mixture is stirred for a short time in the cold and then is allowed to warm slowly to room temperature. Prior to warming, the addition of a small amount of DMPU (approximately 20 mole percent) (1,3-dimethyl-3,4,5,6-tetrahydro-2(1H)pyrimidinone) to the reaction mixture appears to enhance the yield of the product. Stirring is continued for about 30 minutes to about one hour after the mixture has warmed to room temperature to complete the condensation.

The 7β-protected amino-1-carba-3-cephem ester, (2), is recovered from the reaction mixture by extraction into a water immiscible organic solvent. The solution is evaporated and the reaction product mixture dissolved in toluene, a higher boiling glycol ether, chlorobenzene or other inert solvent having a suitable boiling point, and heated at a temperature above about 85° C., preferably above 100° C., for about 15 minutes to about 4 hours to complete the elimination of the phenylsulfinic acid residue, or the phenylsulfonic acid residue. The solvent is removed and the product is purified by chromatography over a suitable adsorbent such as silica gel. When the process is carried out on a small scale, the product may be purified by HPLC or by preparative thick layer chromatography.

The 7β-protected amino-1-carba-3-cephem ester product (2) can then be deprotected and reacylated with a desired carboxylic acid or an active derivative thereof, to provide a 1-carba(dethia)cephalosporin antibiotic.

The amino-protected-azetidin-2-one (AA) utilized in the preparation of these 1-carba(dethia)cephalosporin substrates, is prepared as shown below in Scheme 1 by the cycloaddition of the imine (formed with benzylamine and 3-t-butyldimethylsilyloxy)propionaldehyde) with the chiral auxiliary 4(S)-phenyl-1,3-oxazolidin-2-one-3-ylacetyl chloride (step 1). (For a description of the preparation of this chiral auxiliary, see Evans and Sjogren, *Tetrahedron Letters*, Vol. 26, No. 32, pp. 3783–3786, 1985.) The imine is formed in dry toluene in the presence of a drying agent such as molecular sieves or via azeotropic distillation of water. The chiral oxazolidinone acetyl chloride then is allowed to react with the previously prepared imine in methylene chloride at a temperature between about −80° C. and about −15° C. in the presence of a tertiary amine such as triethylamine. The cycloaddition product (a), N-benzyl-3β-[(4S)-phenyl-1,3-oxazolidin-2-one-3-yl]-4β-(2-t-butyldimethylsilyloxyethyl)azetidin-2-one, is reduced with lithium in ammonia containing t-butyl alcohol (step 2) to remove the chiral auxiliary and the N-benzyl group to provide (b) the 3β-amino-4β-(2-t-butyldimethylsilyloxyethyl)azetidin-2-one. The β-amino group is protected (step 3) with a suitable conventional amino-protecting group such as the t-butyloxycarbonyl group (tBOC). The amino-protected azetidinone (c) is reacted (step 4) in an inert solvent at a temperature of about 0° C. to about room temperature with tetra(n-butyl)ammonium fluoride to cleave the silyl ether and form 3β-protected amino-4β-(2-hydroxyethyl)azetidin-2-one (d). The hydroxy group is converted in step 5 to the mesylate, triflate, or tosylate ester (e) with methanesulfonyl chloride, trifluoromethylsulfonyl chloride, or tosyl chloride in the presence of a tertiary amine such as triethylamine or pyridine. In step 6 the ester is reacted in acetone at room temperature with sodium iodide or sodium bromide to form the 4-(2-haloethyl)azetidin-2-one (AA) (T=Cl or Br). Preferably the 4-(2-iodoethyl)azetidinone is employed in the process for preparing compounds represented by Formula (2).

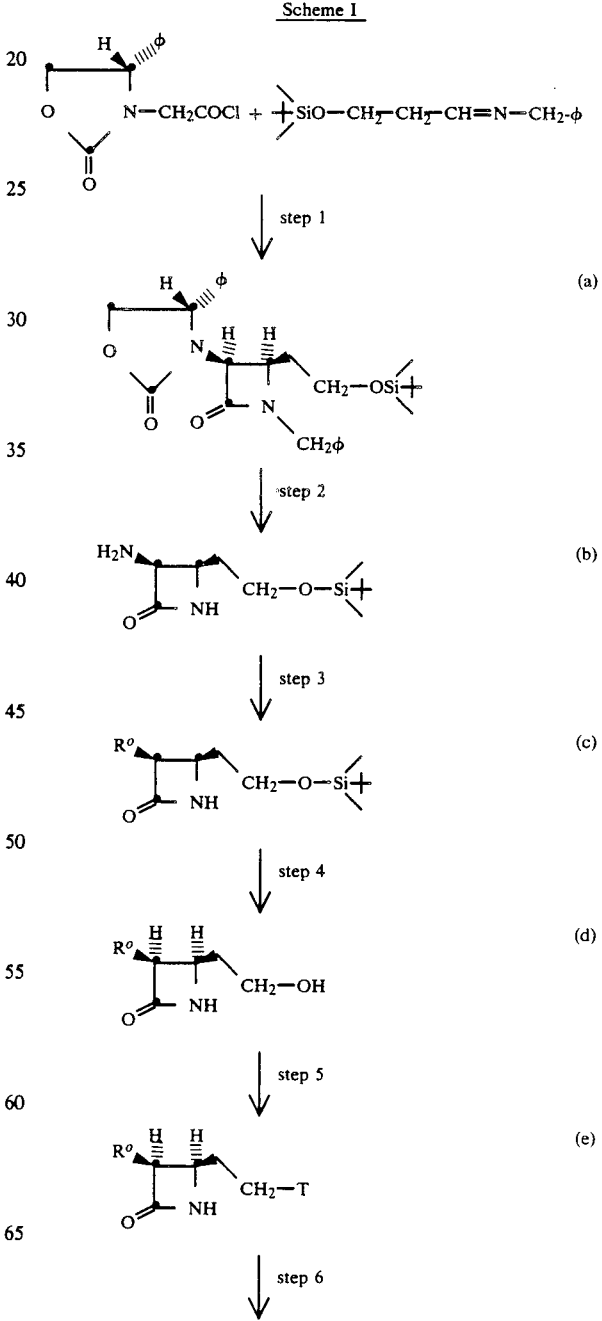

Scheme 1

-continued
Scheme 1

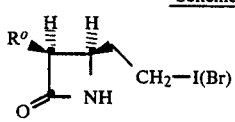
(AA)

In Scheme 1, φ is phenyl; R⁰ is R or R⁴ substituted amino; and

is t-butyldimethylsilyl.

The phenylsulfinyl-substituted or phenylsulfonyl-substituted acrylic acid ester represented by the foregoing Formula (BB) is prepared as shown below in Scheme 2.

In general, an ester of phenylmercaptoacetic acid or a phenylthiomethylketone is alkylated (step 1) with a haloacetic acid ester to form a 3-phenylthio-3-substituted propionic acid ester (aa). Chlorination (step 2) of (aa) with N-chlorosuccinimide in carbon tetrachloride-THF at the reflux temperature provides the 3-chloro-3-phenylthio-3-substituted propionic acid ester (bb).

Dehydrohalogenation (step 3) of (bb) with a strong non-nucleophilic base such as DBU forms the 3-phenylthio-3-substituted acrylic acid ester (cc) as a mixture of the two geometric isomers. For purposes of preparing the 1-carba-3-cephem compounds of the formula 1, the mixture need not be separated into the individual isomers.

In step 4 the phenylthio group of (cc) is oxidized in methylene chloride at room temperature or below with a peracid such as peracetic acid to provide (BB).

The oxidation can be carried out in an inert organic solvent such as methylene chloride. Peracetic acid is best used in preparing the phenylsulfinyl intermediates (Formula (BB), k=1) whereas m-chloroperbenzoic acid can be used to prepare the phenylsulfonyl intermediates (BB) wherein k is 2.

The phenylsulfinyl-substituted intermediates represented by Formula (BB) wherein k is 1 are preferred intermediates in the preparation of 1-carbacephalosporins.

Scheme 2

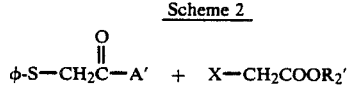

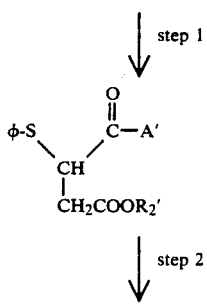
(aa)

-continued
Scheme 2

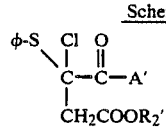
(bb)

step 3

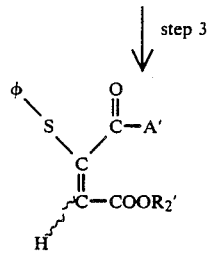
(cc)

step 4

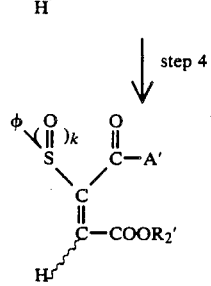
(BB)

In Scheme 2, φ— is phenyl; X is chloro, bromo, or iodo; and A" is typically a group that is inert in the reaction steps outlined in Scheme 2, e.g., groups that will undergo mild peracid oxidation, chlorination with a positive chlorination reagent such as N-chlorosuccinimide, or that are incompatible in the alkylation or dehydrohalogenation steps.

In an example of the preparation of the 3-substituted acrylate (BB) via Scheme 2, methyl phenylmercaptoacetate is alkylated with t-butyl bromoacetate to form t-butyl 3-phenylthio-3-methoxycarbonylpropionate. The diester is chlorinated with N-chlorosuccinimide and the chloro product is reacted with the base DBU to form the unsaturated diester represented by the formula

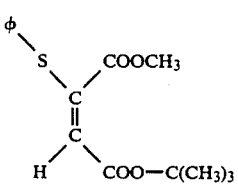

Oxidation of the diester with peracetic acid yields the corresponding phenylsulfinyl ester represented by the above Formula (BB) wherein A" is methoxy and R¹ is t-butyl.

The diester described above is a versatile intermediate which can be converted to a variety of other intermediates represented by (BB). Thus, the t-butyl group can be selectively removed with trifluoroacetic acid (TFA) in the cold to form the mono ester and the free carboxy group re-esterified to form a different mixed diester. For example, the mixed methyl t-butyl diester of the above formula is treated with TFA to form the mono ester of the formula

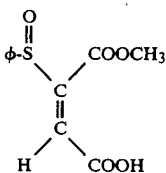

The monoester is then esterified with the desired ester forming group to form a different mixed diester. For example, the free acid is esterified with allyl bromide in the presence of triethylamine to form the mixed methyl allyl diester represented by the formula

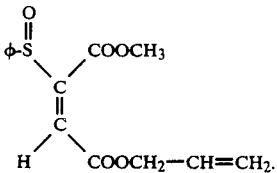

The methyl ester group of the above mixed methyl t-butyl diester sulfide likewise can be selectively deesterified to the mono t-butyl ester and the free carboxy group reesterified to a different mixed diester. Alternatively, the free carboxy group can be converted to another carboxy derivative represented by (A), e.g., an amide, and then used in the cyclization reaction with the intermediate of Formula (AA) to form the corresponding 1-carba-3-cephem represented by Formula (3) wherein R¹ is the carboxy-protecting group R¹ of (BB). Accordingly, the mixed methyl t-butyl diester represented by the formula

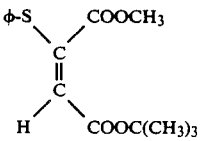

prepared via steps 1 through 3 of Scheme 2 is treated in THF with an equimolar amount of lithium hydroxide to form the mono t-butyl ester represented by the formula

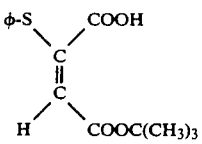

The carboxy group can be reesterified with ester forming reagent or converted to another carboxy derivative such as an acid halide, azide, or amide. Following the reesterification or conversion to a carboxy derivative, the product is oxidized with a peracid to the corresponding phenylsulfinyl or phenylsulfonyl derivative (BB).

In another example of the preparation of a 3-phenylsulfinyl-3-substituted-acrylate (BB), the ketone, phenylthioacetone is alkylated in THF with t-butyl bromoacetate and sodium hydride to yield t-butyl 3-phenylthio-4-oxopentanoate. The keto ester is chlorinated in THF with N-chlorosuccinimide to the 3-chloro keto ester and the latter dehydrohalogenated to t-butyl 3-phe- nylthio-4-oxopent-2-eneoate. The unsaturated keto ester is then oxidized in methylene chloride with peracetic acid to (BB) wherein A" is methyl and R¹ is t-butyl as represented by the following formula

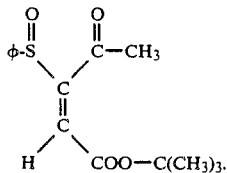

Examples of substituted acrylate esters represented by Formula (BB) which can be obtained by the above-described methods are shown in the following Table 1.

TABLE I

| A" | R¹ |
|---|---|
| —C₂H₅ | t-butyl |
| —OCH₃ | t-butyl |
| —OCH₃ | benzhydryl |
| —CH₂C₆H₅ | t-butyl |
| —O—CH(CH₃)₂ | pNB² |
| —C₆H₅ | pMB¹ |
| —NH₂ | C₂H₅ |
| —OH | CH₃ |
| —N(CH₃)₂ | (CH₃)₃Si |
| —NHC₂H₅ | benzyl |
| —C₄H₉ | (CH₃)₃Si |
| —CH₃ | benzyl |

1/ p-methoxybenzyl
2/ p-nitrobenzyl

The amino-protected 1-carbacephalosporin represented by Formula (3) above can be substituted, deblocked, and N-acylated to provide other 1-carba(dethia)cepyhalosporins.

For example, a 7β-amino-protected-3-acetyl-1-carba-3-cephem ester represented by the formula

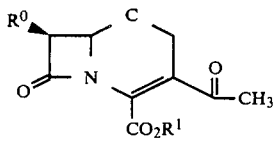

wherein R⁰ and R¹ have the above-defined meanings, which is prepared with intermediate (BB) wherein A' is methyl, is reacted with bromine in the presence of a strong non-nucleophilic base such as LDA (lithium diisopropyl amide) to form the 3-bromoacetyl derivative represented by the formula

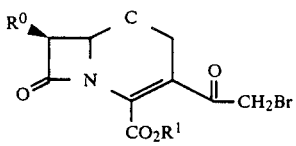

The 3-bromoacetyl ester is reacted with an O, S, or N nucleophile to provide a 3-protected amino 1-carba-3-cephem ester and the latter is deprotected and N-acylated to a compound of Formula (1). For example, the 3-bromoacetyl ester can be reacted with a 5- or 6-membered nitrogen containing heterocyclic thiol or an alkali metal salt thereof to form the compound wherein $R^2$ is the group

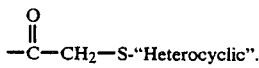

This sequence is further illustrated by the following scheme:

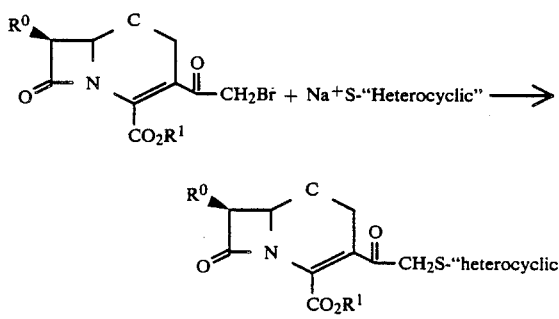

Accordingly, when $R^2$ is $CH_3$, the same sequence can be performed to provide $R^2 = -CH_2-S-$"Heterocyclic".

In the Examples and Preparations, the following abbreviations have the indicated meanings: BSTFA=-bis(trimethylsilyl)trifluoroacetamide; DBU=1,8-Diazabicyclo[5.4.0]undec-7-ene; DMF=dimethylformamide; HPLC=high performance liquid chromatography; t-BOC=t-butyloxycarbonyl; THF=tetrahydrofuran; NMR=Nuclear Magnetic Resonance ($H^1$ spectrum); and J=coupling constant for NMR spectra in Hz.

EXAMPLE 1 p-Nitrobenzyl 7β-(N-phenoxyacetyl-N-(t-butyloxycarbonyl)amino]-3-methyl-3-cephem-4-carboxylate A solution of p-nitrobenzyl-3-methyl-7β-phenoxyacetylamino-3-cephem-4-carboxylate (0.413 g, 1.89 mM, 2.0 equivalents), di-t-butyldicarbonate (0.116 g) -dimethylaminopyridine, and (0.13 ml) triethylamine in ml of $CH_2Cl_2$ was stirred at room temperature for 1 hr. The reaction mixture was then extracted sequentially with cold 1N HCl, brine, and dried over anhydrous sodium sulfate. Removal of the $CH_2Cl_2$ in vacuo followed by silica gel chromatography (toluene/ethyl acetate gradient elution) provided 335 mg (60% yield) of the title compound.

Mass Spectra m/e 583; IR ($CHCl_3$) 1765 cm$^{-1}$ (β-lactam), nmr ($CDCl_3$) δ: 1.56 (s, 9, t-Bu), 2.24 (s, 3 Me), 3.2, 3.4 (AB, J=16 Hz, 2, C(2) protons - $H^7$ to $H_2β$[5-bond] coupling, 5.06 (d, J=4 Hz, 1, $H^6$), 5.21 (s, 2, $PhOCH_2$), 5.31, 5.44 (AB, J=13 Hz, 2, PNB), 5.83 bd, J=4 Hz, 1, $H^7$).

In a procedure analogous to that in Example 1, the following compounds were prepared.

EXAMPLE 2

Methyl 3-methyl-7β-[(N-phenylacetyl, N-t-butoxycarbonyl)amino]-3-cephem-4-carboxylate NMR (60 MHz, $CDCl_3$): δ: 1.50 (s, 9H, t-Bu); 2.15 (s, 3H, 3-methyl); 3.17 (m, 2H, C-2 protons); 3.83 (s, 3, $CO_2CH_3$); 4.25 (s, 2H, φ$CH_2$-; 4.93 (d, J=4 Hz, 1H, $H^6$); 5.73 (d, J=4 Hz, 1, $H^7$).

EXAMPLE 3

Methyl 3-methyl-7β-[(N-acetyl, N-t-butoxycarbonyl)amino]-3-cephem-4-carboxylate

IR ($CHCl_3$) 1775 cm$^{-1}$ (β-lactam carbonyl)
FDMS: 370 m/e
NMR (60 MHz, $CDCl_3$)δ: 1.63 (s, 9H, t-Bu); 2.32 (s, 3, 3-$CH_3$); 2.67 (s, 3H, acetyl); 3.29, 3.58 (AB, J=16 Hz, 2H, C-2 protons); 3.97 (s, 3, $CO_2CH_3$); 5.10 (d, J=4 Hz, 1H, $H^6$): 5.87 (d, J=4 Hz, 1, $H^7$).

EXAMPLE 4 p-Nitrobenzyl 3-methyl-7β-[(N-chloroacetyl, N-butoxycarbonyl)amino]-3-cephem-4-carboxylate IR ($CHCl_3$) 1780 cm$^{-1}$ (β-lactam carbonyl)
FDMS: 529 m/e
NMR (300 MHz, $CDCl_3$) δ: 1.51 (s, 9H, t-Bu); 2.22 (s, 3H, $CH_3$); 3.23, 3.45 (AB, J=16 Hz, 2H, C-2 protons); 4.73 (s, 2H, $CH_2$-Cl); 5.04 (d, J=4 Hz, 1H, $H^6$); 5.29, 5.41 (AB, J=13 Hz, 2H, P-$NO_2$-φ-$CH_2$-); 5.77 (d, J=4 Hz, 1H, $H^7$).

EXAMPLE 5 p-Nitrobenzyl 3-methyl-7β-(N-methoxyacetyl,N-t-butoxycarbonyl)amino]-3-cephem-4-carboxylate IR ($CHCl_3$) 1770 cm$^{-1}$ (β-lactam carbonyl)
FDMS: 507 m/e
NMR (300 MHz, $CDCl_3$) ($\Delta^3$ isomer only); 1.52 (s, 9H, t-Bu); 2.28 (s, 3H, $CH_3$); 3.16, 3.57 (AB, J=16 Hz, 2H, C-2 protons); 3.87 (s, 3H, $-OCH_3$); 5.05 (d, J=4 Hz, 1H, $H^6$); 5.28, 5.44 (AB, J=13 Hz, 2H, p-$NO_2$φ-$CH_2$-); 5.64 (d, J=4 Hz, 1H, $H^7$).

EXAMPLE 6

Benzhydryl 3-acetoxymethyl-7β-[(N-formyl, N-t-butoxycarbonyl)amino]-2-cephem-4-carboxylate FDMS: 566 m/e
NMR (60 MHz, $CDCl_3$ (on $\Delta^2$ only); 1.57 (s, 9H, t-Bu); 2.00 (s, 3H, $CH_3$); 4.68 (s, 2, $-CH_2-O-$acetyl); 5.16 (broad s, 1H, C-4); 5.25 (d, J=4 Hz, 1H, $H^6$); 5.67 (d, J=4 Hz, 1H, H-7); 9.23 (s, 1H, HC(O)).

EXAMPLE 7

2,2,2-Trichloroethyl 3-Methyl-7β-[(N-allyloxycarbonyl, N-t-butoxycarbonyl)amino]-3(2)-cephem-4-carboxylate IR ($CHCl_3$) 1750-1780 cm$^{-1}$ (broad) (β-lactam carbonyl)
FDMS: 528, 530 m/e
NMR (300 MHz, $CDCl_3$) $\Delta^2/\Delta^3$ mixture δ: 1.6 (s, t-Bu); 2.0 (s, 3H, $CH_3$); 3.1, 3.6 (AB, 5H, J=16 Hz, $H^2$ protons); 5.1, 5.3, 5.9 (m, allyl protons); 5.6 (d, J=4 Hz, $H^6$); 5.7 (d, 1H, J=4 Hz, $H^7$); 6.0 (s, 1H, $H^2$ of $\Delta^2$ isomer).

EXAMPLE 8 p-Nitrobenzyl, 3-methyl-7β-[(methoxycarbonyl, butoxycarbonyl)amino]-3-cephem-4-carboxylate Mass spectrum 507 (m/e)

IR 1770 cm$^{-1}$ (β-lactam carbonyl)

NMR (300 MHz CDCl$_3$ 1.52 (s, 9H, t-Bu); 2.28 (s, 3H, CH$_3$—); 3.16, 3.57 (AB, J=16 Hz, 2H, c(2)-protons); 5.05 (d, J=4 Hz, 1H, H$^6$); 5.28, 5.44 (AB, J=13 Hz, 2H, p-NO$_2$—ϕ—CH$_2$—); 5.64 (d, J=4Hz, 1H, H$^7$); 7.63, 8.24 (AB, J=8.5 Hz, 4H, p-NO$_2$-ϕ-CH$_2$—).

EXAMPLE 9

1-(t-Butyldimethylsilyl)-3β-[(N-phenoxyacetyl-N-t-butyloxycarbonyl)amino]-4-(2-t-butyloxycarbonylthiomethyl)-azetidin-2-one (A) Silylation The free-N-H compound (0.636 g, 174 mM), 275 mg (182 mM) of t-butyl dimethylsilyl chloride and 0.25 ml of triethylamine were dissolved in 10 ml of dimethylformamide and allowed to stir at room temperature for 2 days. The reaction mixture was then diluted with ethyl acetate and extracted sequentially with H$_2$O (4 times), and brine (1 time), and dried over anhydrous sodium sulfate. The crude product was evaporated to dryness and used as is in Part B, below.

(B) The product from Part A was dissolved in 15 ml of CH$_2$Cl$_2$ and treated with 757 mg (347 mM) of di-t-butyldicarbonate, 212 mg (173 mM) of dimethylamino pyridine, and 0.24 ml of triethylamine. After stirring for 1 hour, the reaction mixture was diluted with cold ethyl acetate and washed sequentially with cold 1N HCl and brine and dried over anhydrous sodium sulfate. Chromatography on 15 g of Merck silica gel using a gradient elution beginning with 400 ml of toluene and ending with 400 ml of ethyl acetate/toluene (1:1) provided 537 mg (53overall yield) of the title compound.

IR (CHCl$_3$) 1814 cm$^{-1}$ (β-lactam carbonyl)

FDMS: 580, 566 m/e

NMR (60 MHz, CDCl$_3$) δ: 0.37 (s, 3H, Si-CH$_3$); 1.00 (s, 3H, Si-CH$_3$); 1.43, 1.57 (s, 27H, t-butyl), 3.25, 3.58 (AB, J=14 Hz, 2H, CH$_2$-CO$_2$-t-butyl); 5.23 (m, 2H, —O—CH$_2$ϕ); 5.50 (d, J=4 Hz, 1H, H$^4$); 6.08 (d, J=4 Hz, 1H, H$^3$).

EXAMPLE 10

Methyl-3-methyl-7β-(t-butoxycarbonyl)amino-3-cephem-4-carboxylate and methyl-3-methyl-7-(t-butoxycarbonyl)amino-2-cephem-4-carboxylate mixture The product of Example 2 (226 mg) was dissolved in 15 ml of CH$_2$Cl$_2$, cooled to −78° C., and treated with 59 mg of N,N-diethylethylene diamine, utilizing an additional 5 ml of CH$_2$Cl$_2$ as a wash solution to aid quantitative transfer. The reaction mixture was allowed to warm to room temperature and stirred for 38 hours. The crude product mixture was then extracted sequentially with cold 1N HCl and brine, and dried over anhydrous sodium sulfate. The crude product was then chromatographed over 8.0 g of Merck silica using 300 ml of toluene and 300 ml of ethyl acetate in a gradient elution to provide the title compound as a mixture of Δ$^2$+Δ$^3$ isomers (116 mg yield).

IR 1775 cm$^{-1}$ (β-lactam carbonyl)

3350 cm$^{-1}$ (N-H)

NMR (60 MHz, CDCl$_3$) δ: 1.52 (s, t-Bu); 1.92 (s, 3H, Δ$^2$ C$_3$—CH$_3$); 2.33 (s, 3H, Δ$^3$-CH$_3$); 3.20, 3.53 (AB, J=17 Hz, 2H, C$_2$—CH$_2$ for Δ$^3$3.83 (s, 3H, CO$_2$CH$_3$ for Δ$^2$); 3.87 (s, 3H, CO$_2$CH$_3$ for Δ$^3$); 4.73 (Bs, C$_4$—H for Δ$^2$); 4.97 (d, J=4Hz, 2H for Δ$^3$); 5.23 (Bs, 1H, C$_7$—H for Δ$^2$); 5.43 (Bs, 1H, C$_7$H for Δ$^3$); 5.97 (Bs, 1H, C$_2$—H for Δ$^2$).

EXAMPLE 11

7β-3-Methyl-7-(t-butoxycarbonyl)amino-3-cephem-4-p-nitrobenzyl carboxylate and 7β-3-methyl-7-(t-butoxycarbonyl)amino-2-cephem-4-p-nitrobenzyl carboxylate Utilizing the product from Example 1 and a procedure analogous to that of Example 11, the title compound was produced.

71% Δ$^3$/15% Δ$^2$

IR 1770 cm$^{-1}$ (β-lactam carbonyl)

3420 cm$^{-1}$ (N-H)

FDMS: 449 m/e

NMR (300 MHz, CDCl$_3$) δ[Δ$^3$ isomer]: 1.49 (s, 9H, t-Bu); 2.20 (s, 3H, C$_3$—CH$_3$); 3.29, 3.58 (AB, J=18 Hz, 2H, C$_2$-protons); 4.99 (d, J=4Hz, 1H, H$^6$); 5.3–5.5 (m, 3H, p-NO$_2$—C$_6$H$_4$—CH$_2$— and N—H); 5.61 (dd, J=4, 9 Hz, H$^7$).

The following Preparations 1–7 describe the preparation of 1-carba(1-dethia)compounds employed in the process.

PREPARATION OF SUBSTITUTED ACRYLIC ACID ESTERS

Preparation 1

1-Methyl 4-t-butyl 2-phenylsulfinylmaleic acid diester

To a 2-liter, flame-dried flask flushed with nitrogen and equipped with a dropping funnel and stirrer containing bis(trimethylsilyl)lithiumamide (254.23 mmole) in 200 ml of THF and cooled to −42° C. was added a solution of methyl phenylmercaptoacetate (43.33 g, 254.23 mmole) in 100 ml of THF. The solution was stirred in the cold for about 25 minutes and was transferred via cannula over 30 minutes to another flask containing t-butyl bromoacetate (51.08 g, 261.86 mmole) in 100 ml of THF also cooled to −42° C. The reaction mixture was stirred over 2.5 hours while the flask was allowed to warm to room temperature. The reaction mixture was poured into 800 ml of a saturated solution of ammonium chloride in water and 1200 ml of ethyl acetate were added. The organic layer was separated and the aqueous layer was extracted once with 300 ml of ethyl acetate. The extract was combined with the organic layer, dried over magnesium sulfate, filtered and evaporated under vacuum to yield 80 g of the crude product as a brownish oil. The crude product was purified via preparative HPLC to yield 60 g (79.7% yield) of the product, 1-methyl 4-t-butyl 2-phenylthiosuccinic acid diester.

90 MHz NMR (CDCl$_3$, δ): 1.4 (s, 9H, t-butyl ester H), 2.9–3.0 (m, 2H, CH$_2$ H), 3.7 (s, 3H, COOCH$_3$), 3.9 (dd, J=7 and 9, 1H, methine H), 7.5–7.2 (m, 5H, phenyl H).

The mixed diester phenylsulfide product obtained above (60 g, 202.43 mmole) was dissolved in a mixture of 1000 ml of carbon tetrachloride, 500 ml of THF and N-chlorosuccinimide (28.38 g, 212.55 mmole) and the mixture was heated at the reflux temperature for about 4 hours. The thin layer chromatogram run with a small portion of the reaction mixture showed one major spot and no starting material. The mixture was evaporated under vacuum and the residue was treated with hexane.

The insoluble material was filtered, washed with hexane, the hexane wash combined with the hexane filtrate evaporated under vacuum to yield 67 g of -methyl 4-t-butyl 2-chloro-2-phenylthiosuccinic acid diester as an orange oil.

The chloro diester obtained above (67 g, 02.51 mmole) was dissolved in 1 liter of methylene chloride and the solution cooled to −78° C. DBU (31.44 g, 206.56 mmole) was added to this cold solution via syringe and the solution turned dark and thickened. The reaction mixture was allowed to warm to room temperature over 1.5 hours when a thin layer chromatogram of the reaction mixture showed two major spots and no starting material. The mixture was poured into 1 liter of water containing 200 ml of 1N hydrochloric acid and the organic layer separated. The organic layer was again poured into aqueous HCl as before, the organic phase separated, dried over magnesium sulfate, filtered and evaporated under vacuum to yield 60 g of the product as a brownish, oily solid. The crude product was purified via preparative HPLC to yield 47.7 g of 1-methyl 4-t-butyl 2-phenylthiomaleic acid diester as a light yellow oil which solidified upon standing in the refrigerator overnight.

90 MHz NMR (CDCl$_3$, δ): 1.4 and 1.5 (s, 9H, t-butyl H), 3.3 and 3.6 (s, 3H, COOCH$_3$), 5.4 and 6.3 (s, 1H, vinyl H), and 7.2–7.6 (m, 5H, phenyl H).

To a solution of the maleic acid diester obtained above (2.32 g, 7.95 mmole) in 75 ml of methylene chloride and cooled to −42° C. was added peracetic acid (1.67 ml, 8.745 mmole) and the mixture was allowed to warm to room temperature. The reaction mixture was stirred at room temperature for about one hour and 1.95 g of dimethyl sulfide was added. The mixture was stirred for 30 minutes after addition of the sulfide and was then poured onto a pad of silica gel (150 g). The pad was washed with methylene chloride until all remaining starting material had filtered. The pad was then flushed with diethyl ether until the desired product had filtered. The ether solution of the product was evaporated to yield the product as a yellow oil. The oil was treated three times with 200 ml-portions of toluene, and after each treatment was evaporated under vacuum. There were obtained 1.95 g (79% yield) of the 2-phenylsulfinyl maleic acid diester as a yellow oil.

90 MHz NMR (CDCl$_3$, δ): 1.5 and 1.6 (s, 9H, t-butyl), 3.6 and 3.7 (s, 3H, COOCH$_3$), 6.9 and 7.2 (s, 1H, vinyl H), 7.1 and 7.7 (m, 5H, phenyl H).

Preparation 2

1-Methyl 4-allyl 2-phenylsulfinyl maleic acid diester

The methyl t-butyl phenylsulfinyl maleic acid mixed diester obtained as described by Preparation 1 was treated with 8 ml of trifluoroacetic acid at 0° C. to effect selective removal of the t-butyl ester group. After 5 minutes, the reaction mixture was allowed to stir for 2 hours at room temperature and was then evaporated under vacuum at 45° C. to yield an oil. The oil was dissolved in the minimum amount of methylene chloride and the solution was diluted with hexane until cloudy. The product precipitated as a white solid. The mother liquor was decanted from the solid product which was washed with a mixture of 20% methylene chloride/hexane. The washings were added to the mother liquor and placed in the refrigerator overnight to obtain a second crop of product. There were obtained 2.124 g of first crop product and a second crop of 900 mg (79.6% yield) as dried under vacuum.

The phenylsulfinyl half ester obtained as described above (2.124 g, 8.362 mmole) was dissolved in 8 ml of DMF and the solution cooled to 0° C. First, allyl bromide (1.011 g, 8.362 mmole) was added to the solution followed by triethylamine (1.25 ml, 9.0 mmole) and the mixture was allowed to warm to room temperature. The reaction mixture was stirred at room temperature for 2.5 hours, a thin layer chromatogram of a small portion of the reaction mixture indicated that most of the starting material had reacted, and showed a new major spot. The very dark reaction mixture was poured into a mixture of 60 ml of diethyl ether and 50 ml of water. The aqueous layer was separated and washed with 40 ml of diethyl ether. The ether layers were combined and washed sequentially twice with 50 ml-portions of a saturated aqueous sodium bicarbonate solution, twice with 50 ml-portions of 1N hydrochloric acid and once with 50 ml of brine. The washed organic layer was dried over magnesium sulfate, filtered and evaporated under vacuum to yield the product as a yellow oil. The product was taken up in 50 ml of toluene and evaporated under vacuum. The process was repeated to yield 1.934 g (78.6% yield) of the title compound, the allyl methyl diester.

90 MHz NMR (CDCl$_3$, δ) 3.6 (s, 3H, COOCH$_3$)

4.7(dm, J = 6, 2H, allyl CH$_2$), 5.2–5.5(m, 2H, allyl —CH$_2$—C=C),

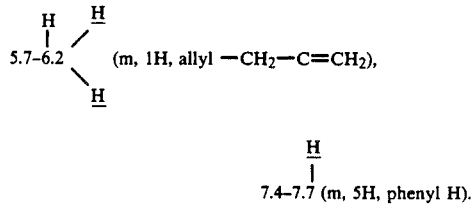

7.4–7.7 (m, 5H, phenyl H).

Preparation 3

1-Ethyl 4-allyl 2-phenylsulfinyl maleic acid diester

To a solution of 1-methyl 4-t-butyl 2-phenylthio maleic acid diester (5 g, 16.99 mmole) in 100 ml of THF was added lithium hydroxide (16.99 mmole) and the mixture was stirred for 3 hours at room temperature. The reaction mixture was poured into a mixture of 150 ml of water and 300 ml of diethyl ether, and the aqueous and organic layers were separated. The aqueous layer was washed twice with 150 ml-portions of diethyl ether and the ether wash was combined with the organic layer and evaporated to yield 2.2 g of the starting material, the diester. The aqueous layer was acidified with 17 ml of 1N hydrochloric acid and extracted twice with 200 ml-portions of diethyl ether. The extracts were combined, dried over magnesium sulfate, filtered and evaporated in vacuum to yield 2.7 g of the mono t-butylester, 4-t-butyl 2-phenylthiomaleic acid mono ester, as a yellow oil (57%).

To a solution of the phenylthio half ester obtained as as described above (8.0 g, 28.551 mmole) in DMF was added via pipette ethyl iodide (4.9 g, 31.406 mmole) and triethylamine (4.78 ml, 34.261 mmole) and the mixture was stirred for one hour at room temperature. The reaction mixture was then heated briefly to a temperature of 65° C. and after cooling, an additional 2.0 ml of ethyl iodide in 4.0 ml of triethylamine were added. The mixture was again heated briefly to a temperature of about 65° C. and was cooled. The reaction mixture was poured into a mixture of 200 ml of diethyl ether in 120 ml of water. The organic layer was separated from the organic layer which was washed twice with 100 ml-portions of a saturated aqueous solution of sodium bicarbonate, twice with 100 ml of 1N hydrochloric acid and once with 100 ml of brine. The organic layer was then dried over magnesium sulfate, filtered and evaporated under vacuum to yield 6.51 g of the phenylthio ethyl t-butyl diester as an oil (74% yield).

90 MHz NMR (CDCl$_3$, δ): 0.9 and 1.1 (t, J=7, 3H, CO$_2$CH$_2$CH$_3$), 1.4 and 1.5 (s, 9H, t-butyl), 3.7 and 4.1 (q, J=7, 2H, —CO$_2$CH$_2$CH$_3$), 5.4 and 6.2 (s, 1H, vinyl H), and 7.2 to 7.6 (m, 5H, phenyl H).

The t-butyl ethyl diester, 6.51 g, was treated at room temperature for 30 minutes with 9 ml of trifluoroacetic acid to effect select deesterification of the t-butyl ester group and provide 5.1 g of 1-ethyl 2-phenylthiomaleic acid monoethyl ester as a yellow oil.

90 MHz NMR (CDCl$_3$, δ): 0.9 and 1.2 (t, J=7, 3H, CO$_2$CH$_2$CH$_3$), 3.7 and 4.1 (q, J=7, 2H, CO$_2$CH$_2$CH$_3$), 5.4 and 6.2 (s, 1H, vinyl H), 7.1-7.6 (m, 5H, phenyl H), and 8.7 (broad s, 1H, COOH).

The half acid ester obtained as described above (5.1 g, 20.222 mmole) was dissolved in 22 ml of DMF and allyl bromide (3.67 g, 30.333 mmole) was added to the solution followed by triethylamine (4.8 ml, 34.38 mmole) and the reaction mixture was allowed to stir for approximately 16 hours. The mixture was poured into a mixture of 100 ml of water and 200 ml of diethyl ether and the organic layer separated from the aqueous layer. The organic layer was washed twice with 100 ml-portions of a saturated aqueous sodium bicarbonate solution, twice with 100 ml-portions of 1N hydrochloric acid and once with 100 ml of brine. The washed layer was then dried over magnesium sulfate, filtered and evaporated under vacuum to yield 5.5 g (93.2% yield) of 1-ethyl 4-allyl 2-phenylthiomaleic acid diester as a yellow oil.

90 MHz NMR (CDCl$_3$, δ): 0.9 and 1.2 (t, J=7, 3H, —CH$_2$CH$_3$), 3.8 and 4.1 (q, J =7, 2H, —CH$_2$CH$_3$), 4.5 and 4. 6 (dm, J=5, 2H, —CH$_2$—CH=CH$_2$), 5.1-5.4 (m,

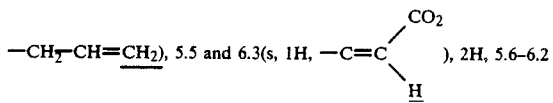

—CH$_2$—CH=CH$_2$), 5.5 and 6.3(s, 1H, —C=C ), 2H, 5.6–6.2

(m, 1H, —CH$_2$—CH=CH$_2$), and 7.2-7.6 (m, 5H, phenyl).

The allyl ethyl diester (5.52 g, 18.891 mmole) prepared as described above was dissolved in methylene chloride and the solution cooled to a temperature of about −42° C. To the cold solution was added peracetic acid (5.04 ml, 26.447 mmole) and the mixture was allowed to stir for about 2.5 hours at room temperature. An additional 2.0 ml of peracetic acid was added and the mixture was stirred at room temperature for an additional 1.5 hours. Dimethylsulfide (4.85 ml, 66 mmole) was then added to the mixture which was stirred for an additional 45 minutes. The unreacted starting material was separated by pouring the reaction mixture directly onto 125 g of silica gel and washing the starting material from the silica with methylene chloride. The silica gel was then eluted with diethyl ether until all of the desired sulfoxide had been washed free. The product containing filtrate was concentrated under vacuum to provide the sulfoxide diester as a yellow oil. The oil was dissolved successively six times in 100 ml-portions of toluene and the evaporated to remove toluene to provide 3.8 g of the sulfoxide diester as an oil (80% yield).

90 MHz NMR (CDCl$_3$, δ): 1.1 and 1.2 (t, J=7, 3H, —CH$_2$CH$_3$), 4.0 and 4.1 (q, J=7, 2H, —CH$_2$CH$_3$), 4.65 and 4.75 (dm, J=5, 2H, —CH$_2$—CH=CH$_2$), 5.1-5.5 (m, 2H, —CH$_2$—CH=CH$_2$), 5.7-6.2 (m, 1H, —CH$_2$—CH=CH$_2$), 6.9 and 7.1 (s, 1H, C=CHCOO), and 7.3-7.9 (m, 5H, phenyl).

Preparation 4 t-Butyl 7β-t-butyloxycarbonylamino-3-methoxycarbonyl-1-carba(dethia)-3-cephem-4-carboxylate A. Preparation of 2-(dimethyl-t-butylsilyloxy)propionitrile To a solution of 2-cyanoethanol (7.0 g, 98.48 mmole) in 75 ml of DMF was added dimethyl-t-butylchlorosilane (16.028 g, 106.36 mmole) followed by imidazole (8.17 g, 120 mmole). The reaction mixture was stirred for about 15 hours and was poured into a mixture of 250 ml of diethyl ether and 200 ml of 1N hydrochloric acid. The ether layer was separated and washed twice with 150 ml of 1N hydrochloric acid. The organic layer was separated, dried over magnesium sulfate, filtered and evaporated under vacuum. The silyl ether product was obtained as an oily residue. The residue was diluted with 100 ml of toluene and the solution evaporated. This procedure was repeated three times to provide 17.26 g of 2-(dimethyl-t-butylsilyloxy)propionitrile as a colorless liquid (94.7% yield).

90 MHz, NMR (CDCl$_3$, δ): 0.1 (s, 6H, methyl H), 0.9 (s, 9H, t-but H), 2.9 (t, J=6, 2H, CH$_2$CN), and 3.8 (t, J=6, 2H, SiO—CH$_2$).

B. 3-(Dimethyl-t-butylsilyloxy)propionaldehyde

To a solution of 3-(dimethyl-t-butylsilyloxy)propionitrile (6.04 g, 32.65 mmole) in 50 ml of THF and cooled to a temperature of 0° C. was added with a syringe, di-isobutylaluminum hydride (60 mmole in 60 ml of THF) and the mixture was allowed to warm to room temperature. After a thin layer chromatogram of the reaction mixture indicated that very little reaction had occurred, the reaction mixture was heated to reflux for a few minutes. The reaction mixture was then cooled to room temperature and poured into a stirred mixture of 150 ml of 1M tartaric acid and 200 ml of diethyl ether. Some gas evolution occurred and the mixture was transferred to a separatory funnel with diethyl ether. The ether layer was separated, dried with magnesium sulfate, filtered, and evaporated in vacuo. The liquid residue containing some suspended solids was diluted with hexane, filtered and the precipitate washed with hexane. The filtrate and washings were concentrated in vacuo to provide 3.7 g of the silyloxy propionaldehyde as a light yellow liquid (60.3% yield). The NMR spectrum indicated the product to be about 75% pure and contaminated with some starting material and silanol.

90 MHz, NMR (CDCl$_3$, δ): 0.2 (s, 6H, methyl H), 0.8 (s, 9H, t-but H), 2.5 (dt, J=2.5, 6, 2H, CH$_2$CO), 3.9 (t, J=6, 2H), and 9.5 (t, J=2.5, 1H, COH).

C. Imine Formed With Benzylamine and 3-(Dimethyl-t-butylsilyloxy)propionaldehyde To a solution of the silyloxypropionaldehyde prepared as described in B. above (2.5 g, 13.3 mmole) in about 20 ml of toluene were added benzylamine (10.64 mmole, 1.16 ml) and about 3–4 g of 4A molecular sieves. The mixture was occasionally swirled gently over 25 minutes to form the imine of the silyloxyaldehyde and benzylamine.

D. N-Benzyl-3β-[(4S)-phenyl-1,3-oxazolidin-2-one-3-yl]-4β-(2-dimethyl-t-butylsilyloxyethyl)azetidin-2-one To a solution of (4S)-phenyl-1,3-oxazolidin-2-one-3-yl acetic acid (2.2 g, 9.95 mmole) in 20 ml of toluene were added 1.45 g (11.44 mmole) of oxalyl chloride. The yellow solution was stirred for one hour and was then evaporated to provide the corresponding acid chloride as a yellow oil. The acid chloride was dissolved in 20 ml of methylene chloride and the solution was cooled to a temperature of about −78° C. Triethylamine (14.93 mmole, 2.08 ml) was added to the solution of the acid chloride and the solution was stirred for a few minutes at room temperature. The solution of the imine prepared as described above in C. was added to the acid chloride solution via cannula and the reaction mixture was allowed to slowly warm to a temperature of about 15°–20° C. over 2 hours. The reaction mixture was then poured into a mixture of 30 ml of methylene chloride and 30 ml of 1N hydrochloric acid and the organic layer was separated. The organic layer was washed with 40 ml of an aqueous saturated sodium bicarbonate solution and with 40 ml of water and was dried over magnesium sulfate, filtered, and evaporated under vacuum. The azetidinone was obtained as a reddish oil. The oil was chromatographed over 100 g of silica gel using 35% ethyl acetate/hexane for elution. The desired fractions were combined and concentrated in vacuo to a light pink solid. The solid was washed with hexane to remove the color and to yield 1.03 g of the azetidinone as a white solid (21.5% yield).

$[\alpha]_D^{25} = +79.2°$

Mass spectrum: (M+) 480; (M+-t-butyl) 423.

IR 1750 cm$^{-1}$ (β-lactam)

Elemental analysis calculated for $C_{27}H_{36}N_2O_4Si$:

| Theory | Found |
|---|---|
| C, 67.47 | C, 67.61 |
| H, 8.55 | H, 8.78 |
| N, 5.83 | N, 6.03 |

90 MHz, NMR (CDCl$_3$, δ): 0.0+0.25 (2s, 6H, methyl H), 0.8 (s, 9H, t-but H), 1.6 (m, 2H, CH$_2$ H), 3.5 (t, J=6, 2H, SiOCH$_2$ H), 3.8 (dt, J=5 and 6,1H, C$_4$H), 7.1 to 7.5 (m, 10H, phenyl H).

E. 3β-t-Butyloxycarbonylamino-4β-(2-dimethyl-t-butylsilyloxyethyl)azetidin-2-one To 430 ml of liquid ammonia was added 2.385 g (343.71 mmole) of lithium washed with hexane and the mixture was stirred for about 20 minutes to dissolve the lithium. A solution of the N-benzylazetidinone prepared as described above in D. in 87 ml of THF containing 8.496 g (114.49 mmole, 10.8 ml) of t-butanol was added to the lithium-ammonia solution and the mixture was stirred vigorously for 50 minutes. A mixture of methyl alcohol-toluene (87 ml, 1:1) was added to the mixture followed by 21.7 ml of acetic acid. The ammonia was distilled off and the residue was acidified to pH 5 by the addition of 45 ml of acetic acid. A mixture of isopropyl alcohol in chloroform (500 ml, 25%) was added to the concentrate followed by 300 ml of a saturated aqueous sodium bicarbonate solution to adjust the pH of the mixture to pH 9. The organic layer was separated and the aqueous layer was washed twice with 200 ml of 25% isopropyl alcohol in chloroform. The washes were combined with the organic layer, dried over magnesium sulfate, filtered, and concentrated in vacuo to yield 9.3 g of crude 3β-amino-4β-(2-dimethyl-t-butylsilyloxyethyl)azetidin-2-one. The crude 3-amino compound was dissolved in 50 ml of methylene chloride and 8.486 g (38.88 mmole, 8.486 ml) of di-t-butyl-dicarbonate were added to the solution. The mixture was allowed to stir overnight and was then evaporated under vacuum to yield 14.67 g of the 3β-t-butyloxycarbonylamino acylation product. The product was chromatographed on 150 g of silica gel using ethyl acetate/hexane, 50/50 for elution. The fractions containing the desired product were combined and evaporated in vacuo to yield 11.88 g of 3β-t-butyloxycarbonylamino-4-(2-dimethyl-t-butylsilyloxyethyl)azetidin-2-one.

90 MHz, NMR (CDCl$_3$, δ): 0.0 (s, 6H, methyl H), 0.8 (s, 9H, t-but H), 1.4 (s, 9H, t-butyloxy H), 1.7 (m, 2H, CH$_2$ H), 3.6 (t, J=5, 2H, CH$_2$ H), 3.9 (m, 1H, C$_4$H), 5.0 (dd, J=5 and 9, 1H, C$_3$H), 5.5 (d, J=9, 1H, amide H), and 6.2 (broad s, 1H, NH).

F. 3β-t-Butyloxycarbonylamino-4-(2-hydroxyethyl)azetidin-2-one

To a solution of t-butyloxycarbonylaminoazetidinone prepared as described in E. above (11.88 g, 34.48 mmole) in 12 ml of THF was added at 0° C. tetrabutylammonium fluoride (10.412 g, 39.5 mmole) and the mixture was allowed to stir for about 1.5 hours. The reaction mixture was evaporated under vacuum to obtain the product as an oil. The oil was filtered through 100 g of silica gel using 10% ethyl alcohol in ethyl acetate. The filtrate was evaporated under vacuum to provide the product as a yellow solid. The solid was mixed with hexane, sonicated, and filtered to yield 6.28 g of the 4β-(2-hydroxyethyl)azetidinone as a white solid (79.5% yield). The product was shown to be pure cis isomer by its NMR spectrum.

90 MHz, NMR (CDCl$_3$, δ): 1.4 (s, 9H, t-butyloxy), 1.7 (m, 2H, CH$_2$ H), 3.0 (broad s, 1H, OH H), 3.7 (m, 2H, CH$_2$ H), 3.9 (m, 1H, C$_4$H), 5.0 (dd, J=5 and 8,1H, C$_3$H), 5.8 (d, J=8, 1H, amide H), and 6.8 (broad s, 1H, NH).

G. 3β-t-Butyloxycarbonylamino-4β-[2-(methylsulfonyloxy)ethyl]azetidin-2-one

To a solution of the 2-hydroxyethyl substituted azetidinone, prepared as described in F. above (6.28 g, 27.424 mmole) in a mixture of 200 ml of chloroform and 100 ml of dioxane were added triethylamine (11.1 g, 109.7 mmole) and methanesulfonyl chloride (6.283 g, 54.85 mmole). The reaction mixture was stirred for one hour and was then poured into a mixture of 300 ml of methylene chloride and 150 ml of a saturated sodium bicarbonate solution. The organic phase was separated and the aqueous phase was washed twice with 150 ml of methylene chloride. The washes and the organic layer were combined, dried over magnesium sulfate, filtered and evaporated under vacuum to yield an oily solid. The solid was triturated with a mixture of diethyl ether and hexane, 50/50, filtered, dried to yield 8.4 g of the corresponding methanesulfonyloxy derivative.

H. 3β-t-Butyloxycarbonylamino-4β-(2-iodoethyl)azetidin-2-one

A solution of 8.4 g of the mesylate ester prepared as described in G. above (27.3 mmole) in 400 ml of acetone and containing sodium iodide (16.5 g, 110.0 mmole) was heated at the reflux temperature for 4 hours. Another 2 g of sodium iodide were added and the mixture was heated at the reflux temperature for an additional hour. The reaction mixture was evaporated under vacuum and the residue treated with methylene chloride. The insoluble material was filtered and the filtrate was concentrated under vacuum to a brownish oil. The oil was dissolved in 80% ethyl acetate/hexane and filtered through 200 g of silica gel. The filtrate was evaporated to yield 7.65 g of the product as a yellowish solid. The solid was dissolved in the minimum amount of hot ethyl acetate and the warm solution diluted with hexane. The product precipitated to yield 4.9 g of a first crop of the 2-iodoethyl compound as a white solid and 1.65 g as a second crop (70.6% yield).

90 MHz NMR (CDCl$_3$, $\delta$): 1.4 (s, 9H, t-butyloxy H), 2.1 (m, 2H, CH$_2$ H), 3.1 (t, J=5, 2H, CH$_2$I H), 3.9 (dt, J=5 and 7,1H, C$_4$H), 5.1 (m, 2H, C$_4$H and amide H), and 6.2 (broad s, 1H, NH).

$D^{25}[\alpha]=+50.65$

IR (CHCl$_3$) 1770 cm$^{-1}$ ($\beta$-lactam carbonyl).

Elemental analysis calculated for C$_{10}$H$_{17}$N$_2$O$_3$I:

|   | Theory | Found |
|---|--------|-------|
| C | 35.31  | 35.52 |
| H | 5.04   | 4.74  |
| N | 8.24   | 8.08  |

I. t-Butyl 7$\beta$-t-butyloxycarbonylamino-3-methoxycarbonyl-1-carba-3-cephem-4-carboxylate To a 50 ml round bottom flask, flame dried and flushed with dry nitrogen, was added the 2-iodoethylazetidinone prepared as described above in H. (1.0 g, 2.941 mmole) and THF and the solution was cooled to a temperature of about −78° C. To the cold solution was added di-(trimethylsilyl)lithiumamide (2.82 ml, 2.822 mmole) and the mixture was stirred in the fold for about 30 minutes. Next, via cannula, was added 2-phenylsulfinylmaleic acid 1-methyl 4-t-butyl diester (0.927 g, 2.985 mmole) and the reaction mixture was stirred for about 10–15 minutes. 1,3-Dimethyl-3,4,5,6-tetrahydro-2-(1H)-pyrimidinone was added to the reaction mixture which then was allowed to warm slowly to room temperature over about 2 hours. The reaction mixture was stirred at room temperature for about 45 minutes, poured into a mixture of 50 ml of an aqueous ammonium chloride solution and 150 ml of ethyl acetate. The organic phase was separated, dried over magnesium sulfate, filtered and evaporated under vacuum to a yellow oil. The oil was chromatographed on 100 g of silica gel using 25% ethyl acetate/hexane for elution. The fractions containing the desired product were combined and evaporated under vacuum to yield 560 mg of the product as a white foam. NMR indicated the product to be about 80% pure. The product was further purified on preparative thick layer plates (4×2 mm) using 25% ethyl acetate in hexane to give 520 mg of the title compound in about 90% purity.

90 MHz NMR (CDCl$_3$, $\delta$): 1.4 (s, 9H, t-butyl H), 1.5 (s 9H, t-butyl H), 3.7 (s, 3H, COOCH$_3$ H), 3.9 (m, 1H, C$_6$H), 4.9–5.1 (m, 2H, C$_7$H and amide H).

Mass Spec. 396 (M+), 340 (M+- C$_4$H$_8$).

IR (CHCl$_3$, $\delta$) 1781 cm$^{-1}$ $\beta$-lactam carbonyl

Elemental analysis calculated for C$_{19}$H$_{28}$N$_2$O$_7$

|   | Theory | Found |
|---|--------|-------|
| C | 57.56  | 57.63 |
| H | 7.12   | 6.84  |
| N | 7.07   | 7.08  |

Preparation 5

7$\beta$-Phenoxyacetylamino-3-methoxycarbonyl-1-carba(-dethia)-3-cephem-4-carboxylate A portion of t-butyl 7$\beta$-t-butoxycarbonylamino-3-methoxycarbonyl-1-carba(dethia)-3-cephem-4-carboxylate is treated with trifluoroacetic acid at 0° C. to provide 7$\beta$-amino-3-methoxycarbonyl-1-carba(dethia)-3-cephem-4-carboxylic acid trifluoroacetic acid salt. This material is dissolved in tetrahydrofuran and treated with 5 molar equivalents of pyridine followed by 1.25 molar equivalents of phenoxyacetylchloride to provide the title compound.

Preparation 6

Benzhydryl 7$\beta$-Phenoxyacetylamino-3-methoxycarbonyl-1-carba(-dethia)-3-cephem-4-carboxylate A portion of the material from Preparation 4 is dissolved in acetonitrile and treated with diphenyldiazomethane to provide the title compound which is, in turn, used in Example 13.

Preparation 7 p-Nitrobenzyl 7$\beta$-phenoxyacetylamino-3-isopropoxycarbonyl-1-carba(dethia)-3-cephem.-4-carboxylate A. 1-Isopropyl 4-p-nitrobenzyl 2-phenylsulfinylmaleic acid diester The diester is prepared in a manner analogous to Preparation 3 while esterifying the 1-carboxylic acid with isopropanol using dicyclobenzylcarbodiimide and dimethylamino pyridine.

B. t-Butyl-7$\beta$-t-butoxycarbonylamino-3-isopropoxycarbonyl-1-carba(dethia)-3-cephem-4-carboxylate The cyclocondensation to provide this compound is prepared in a manner analogous to Preparation 4(I).

C. Selective deprotection and reprotection

The compound produced in part B is treated with trifluoroacetic acid to provide 7$\beta$-amino-3-isopropoxycarbonyl-1-carba(dethia)-3-cephem-4-carboxylic acid. This compound is then acylated with phenoxyacetyl chloride as in Preparation 5 and esterified with 1.25 molar equivalents of p-nitrobenzylbromide in the presence of 1.5 molar equivalents of N-methylmorpholine in dimethylformamide to provide the title compound which, in turn, is used directly in Example 14.

EXAMPLE 12

Benzhydryl 7$\beta$-(N-t-butoxycarbonyl)amino-1-carba(dethia)-3-cephem-3-methoxycarbonyl-4-carboxylate (A) A 1.96 g sample of benzhydryl 7$\beta$-phenoxyacetyl amino-1-carba(dethia)-3-cephem-3-methoxycarbonyl-4-carboxylate was dissolved in 10 ml of CH$_2$Cl$_2$ and treated with 490 mg of dimethylamino pyridine and 1.07 ml of di-t-butyl dicarbonate. Upon completion of the reaction, the crude mixture was diluted with 300 ml of ethyl acetate and washed sequentially with 1N HCl (2 times), saturated sodium bicarbonate, brine, and dried over anhydrous magnesium carbonate.

NMR (300 MHz, CDCl$_3$): $\delta$: 1.3, 1.8, 2.2 and 2.9 (m, 4H, C$_1$—H. and C$_2$—H); 1.5 (s, 9H, t-butyl); 3.2 (s, 3H, —OCH$_3$); 3.8 (m, 1H, C$_6$), 5.15 (s, 2H, $\phi$-O-CH$_2$—) 5.8 (d, J=7 Hz, 1H, C$_7$—H) 6.9, 7.1 and 7.4 (m, 15H, $\phi_2$-CH— and $\phi$-O—); 7.15 (s, 1H, $\phi_2$-CH—).

Yield=2.29 g.

(B) The imide produced in Step A was dissolved in 35 ml of tetrahydrofuran and treate with 2.68 ml of 1N lithium hydroxide. After stirring for 30 minutes, an additional 0.89 ml of 1N lithium hydroxide was added. Finally, after an additional 30 minutes of stirring, an additional 0.35 ml of lithium hydroxide was added. After 30 minutes, the reaction mixture was diluted with 300 ml of ethyl acetate and extracted sequentially with saturated sodium bicarbonate solution (3 times), brine, and dried over anhydrous magnesium sulfate. Chromatography over 200 g of normal phase silica gel (5% ethyl acetate/$CH_2Cl_2$) yielded 0.91 g of the title compound.

NMR (300 MHz, $CDCl_3$)δ: 1.45 (s, 9H, t-butyl); 1.5, 2.2, 2.3 and 2.9 (m 4H, $C_1$—H and $C_2$—H); 3.3 (s, 3H, —$OCH_3$); 3.9 (m, 1H, $C_6$—H); 5.05 (bd, J=6 Hz, 1H, t-butoxycarbonyl-N—H); 5.3 (m, 1H, $C_7$—H); 7.1 (s, 1H ($C_6H_5$)$_2$—C—H): 7.4 (m, 10H,($C_6H_5$—)$_2$).

EXAMPLE 13 p-Nitrobenzyl 7β-(N-t-butoxycarbonyl)amino-1-carba(dethia)-3-cephem-3-isopropoxycarbonyl-4-carboxylate In a procedure analogous to that of Example 13, the title compound was produced in 57% overall yield.

NMR (300 MHz, $CDCl_3$) δ: 1.2 (d, J=7Hz, 6H, —$CHCH_3$); 1.42 (s, 9H, t-butyl); 1.45, 2.15, 2.3 and 2.85 (m, 4H, $C_1$—H and $C_2$—H), 3.9 (m, 1H, $C_6$—H); 5.05 (heptet, J=7 Hz, 1H, —CH($CH_3$)$_2$); 5.0 (bm, 1H); 5.2 (bm, 1H); 5.4 (AB, J=15 Hz, 2H, —$CH_2$—$C_6H_4$—$NO_2$); 7.6 (d, J=9 Hz, 2H); 8.2 (d, J=9 Hz, 2H).

EXAMPLE 14

1-(1-Methoxyoarbonyl-2-methylprop-1-ene-1-yl)-3β-(t-butoxycarbonyl)amino-1-yl azetidin-2-one A solution of 1-(1-methoxycarbonyl-2-methylprop-1-ene-1-yl)-3β-(phenoxyacetyl)amino-1-yl azetidin-2-one in THF is treated with 1.2 molar equivalents of di-t-butyldicarbonate, 1.0 molar equivalent of triethylamime, and 0.05 molar equivalent of dimethylamino pyridine to provide 1-(1-methoxycarbonyl-2-methylprop-1-ene-1-yl)-3β-(t-butoxycarbonyl, phenoxyacetyl)amino-1-yl azetidin-2-one.

The disubstituted compound from above is then treated with lithium hydroxide in THF to provide the title compound.

We claim:

1. A compound of the formula

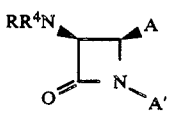

wherein $R^4$ is phenoxyacetyl, phenylacetyl, $C_1$ to $C_6$ alkanoyl or chloroacetyl; wherein R is allyloxycarbonyl, t-butoxycarbonyl, naphthyloxycarbonyl, trichloroethyloxycarbonyl, or p-nitrobenzyloxycarbonyl; A is $C_1$ to $C_6$ alkyl, $C_1$ to $C_6$ substituted alkyl or a group of the formula —S($C_1$-$C_4$ alkyl)$CO_2R'$, wherein R' is hydrogen or a carboxy-protecting group; and A' is hydrogen or an amide-protecting group.

2. A compound of claim 1 wherein R is t-butoxycarbonyl.

3. A compound of claim 2 wherein $R^4$ is phenoxyacetyl.

* * * * *